(12) United States Patent
Torres

(10) Patent No.: US 9,707,309 B2
(45) Date of Patent: Jul. 18, 2017

(54) DISPENSER FOR AIR FRESHENER CONTAINERS

(71) Applicant: L & D S.A.U., Huercal de Almeria (ES)

(72) Inventor: David Fernandez Torres, Huercal de Almerica (ES)

(73) Assignee: L & D S.A.U., Huercal de Almeria (ES)

( * ) Notice: Subject to any disclaimer, the term of this patent is extended or adjusted under 35 U.S.C. 154(b) by 195 days.

(21) Appl. No.: 14/651,778

(22) PCT Filed: Jan. 24, 2013

(86) PCT No.: PCT/ES2013/000015
§ 371 (c)(1),
(2) Date: Jun. 12, 2015

(87) PCT Pub. No.: WO2014/114820
PCT Pub. Date: Jul. 31, 2014

(65) Prior Publication Data
US 2015/0314031 A1    Nov. 5, 2015

(51) Int. Cl.
*A61L 9/12* (2006.01)
*A01M 1/20* (2006.01)
(52) U.S. Cl.
CPC .......... *A61L 9/127* (2013.01); *A01M 1/2044* (2013.01); *A61L 9/12* (2013.01)
(58) Field of Classification Search
CPC .......... A61L 9/12; A61L 9/127; A01M 1/2044
(Continued)

(56) References Cited

U.S. PATENT DOCUMENTS 3,169,705 A  *  2/1965  Geiger  ............... A01M 1/2044
                                                    239/34
4,621,768 A  *  11/1986  Lhoste  .................. A61L 9/127
                                                    239/44
(Continued)

FOREIGN PATENT DOCUMENTS

DE    10 2010 026 849 A1    1/2012
WO    WO 01/82982 A1        11/2001
WO    WO 2014/114820 A1     7/2014

OTHER PUBLICATIONS

PCT International Preliminary Report (English Translation) dated Jul. 28, 2015 corresponding to PCT International Application No. PCT/ES2013/000015; 2 Pages (Patent Publication No. WO 2014/114820 A1).

(Continued)

*Primary Examiner* — Arthur O Hall
*Assistant Examiner* — Joseph A Greenlund
(74) *Attorney, Agent, or Firm* — Daly, Crowley, Mofford & Durkee, LLP

(57) ABSTRACT

The dispenser can be used with air fresheners including a container (1) holding a perfuming liquid (2) and closed by means of a wooden cap (3), with the particularity that the said wooden cap (3) is provided with a central axial duct (4) of small diameter, communicating with a second transverse duct (5) provided in an upper semi-cylindrical extension (6) and passing through this transverse duct (5), the diffusing string or wick (7) being retained therein and impregnated in perfuming liquid (2) when the container (1) with the cap (3) coupled to the neck (1') is turned upside down.

2 Claims, 4 Drawing Sheets

(58) Field of Classification Search
USPC .................. 239/34–60; 43/1, 131, 132.1
See application file for complete search history.

(56) References Cited

U.S. PATENT DOCUMENTS

| | | | | | |
|---|---|---|---|---|---|
| 4,655,355 | A | * | 4/1987 | Turoff | B29C 49/20 215/48 |
| 4,742,960 | A | * | 5/1988 | Bustillo | A61L 9/12 239/47 |
| 4,858,776 | A | * | 8/1989 | Mehra | B65D 41/28 215/270 |
| 5,746,019 | A | * | 5/1998 | Fisher | A01M 31/008 239/145 |
| 5,755,381 | A | * | 5/1998 | Yazaki | A61L 9/12 239/43 |
| 6,755,351 | B2 | * | 6/2004 | Giovannone | A61L 9/12 239/34 |
| 6,923,383 | B1 | * | 8/2005 | Joshi | A01M 1/2072 239/302 |
| 7,481,380 | B2 | * | 1/2009 | Kvietok | A01M 1/2044 239/301 |
| 7,614,568 | B2 | * | 11/2009 | Joshi | A61L 9/037 222/386.5 |
| 7,643,735 | B1 | * | 1/2010 | Mast | A01M 1/2077 222/146.5 |
| 7,997,508 | B2 | * | 8/2011 | Motylinski | A61L 9/127 215/355 |
| 8,292,196 | B2 | * | 10/2012 | Varanasi | A01M 1/2044 239/145 |
| 8,960,566 | B2 | * | 2/2015 | Leung | A45D 34/02 239/145 |
| 2003/0071137 | A1 | * | 4/2003 | Giovannone | A61L 9/12 239/34 |
| 2005/0211790 | A1 | * | 9/2005 | Kvietok | A61L 9/127 239/44 |
| 2006/0097066 | A1 | * | 5/2006 | Kvietok | A01M 1/2044 239/44 |
| 2006/0231641 | A1 | * | 10/2006 | Uchiyama | A01M 1/2044 239/34 |
| 2006/0233538 | A1 | * | 10/2006 | Tollens | A01M 1/2072 392/390 |
| 2006/0237555 | A1 | * | 10/2006 | Cetti | A01M 1/2044 239/54 |
| 2011/0192912 | A1 | * | 8/2011 | Herd | A61L 9/127 239/44 |
| 2015/0096218 | A1 | * | 4/2015 | Burr | A01M 31/008 43/1 |

OTHER PUBLICATIONS

PCT Written Opinion of the ISA (English Translation) dated Oct. 10, 2013 corresponding to PCT International Application No. PCT/ES2013/000015; 5 Pages (Patent Publication No. WO 2014/114820 A1).

PCT International Search Report (with English Translation) dated Oct. 10, 2013 corresponding to International Application No. PCT/ES2013/000015; 7 Pages (Patent Publication No. WO 2014/114820 A1).

* cited by examiner

DISPENSER FOR AIR FRESHENER CONTAINERS

CROSS REFERENCE TO RELATED APPLICATION

This application is a U.S. National Stage of PCT application PCT/ES2013/000015 filed on Jan. 24, 2013, and entitled "DISPENSER FOR AIR FRESHENER CONTAINERS," which application is hereby incorporated herein by reference in its entirety.

OBJECT OF THE INVENTION

This invention relates to a dispenser for air freshener containers, specifically intended to dispense the perfume inside an air freshener container and which may be used, for example, in a vehicle, a small enclosed space such as a toilet room, etc.

The object of the invention is to provide maximum efficiency with regard to the amount of perfume required to perfume an atmosphere.

BACKGROUND OF THE INVENTION

The prior art includes many types of air freshener containers holding perfume and complemented by a cap associated with a liquid or perfume diffuser wick, the wick logically protruding out of the container, more specifically through the cap provided on the same.

In any case, the liquid or perfume inside a container of the type conventionally used for air fresheners is provided with at least one portion of string or diffuser wick inside the container, that is, constantly immersed in the liquid, thus impregnating the said diffuser wick all at once, with no gradual dispensing, so that when the container is turned upside down in order to impregnate the diffuser wick with the perfume, the impregnation not only occurs all at once but the perfumed liquid may also impregnate the outside of the cap.

Also, in the case of conventional air fresheners the cap is not hermetically sealed onto the container, so that on turning the container upside down part of the perfuming liquid flows through the space between the cap thread and the thread on the neck of the container, and subsequently, when the container is hung for use, the said part or small amount of liquid accidentally flowing between the thread of the cap and the thread of the container neck may seep out and stain the part or surface on which the air freshener unit is located, so that if it is hung inside a car cabin, for example, it may stain the seat, the dashboard, etc., and if hung in a toilet room it may stain part of the same.

Air fresheners whose structural and functional features are subject to the aforementioned problems are described in European patent EP 1 278 556 B1, and also in PCT no. WO 00/67807.

DESCRIPTION OF THE INVENTION

The proposed dispenser for air freshener containers has been designed to solve all the problems referred to in the above section, on the basis of a simple but highly efficient solution.

More specifically, the dispenser to which the invention relates is applicable to the type of air freshener which includes a container holding a perfuming liquid and a wooden cap screwed onto the neck of the container itself, these features being the basis for the novelty of the invention, which consists of the wooden cap being provided with a central axial duct, having a small diameter, the outer part of the said duct opening onto another transverse hole made for this purpose in an external semi-cylindrical extension, in which a string acting as a diffuser wick is fixed, so that when the container with the wooden cap coupled to it is turned upside down the liquid flows through the axial duct in the cap to the duct in the upper semi-cylindrical part and thus to the diffuser string or wick itself, the latter becoming impregnated with perfuming liquid, gradually and in such a way as to prevent the liquid from seeping out, so that each time the container with the aforementioned device is turned upside down the perfuming liquid is gradually dispensed in a perfectly controlled manner, more or less liquid being dispensed in accordance with the diameter of the axial duct in the cap.

The device is also complemented by a plastic stopper hermetically sealing the container when the air freshener unit is not in use, so that when the said air freshener is used, that is, when it is turned upside down in order to impregnate the diffuser wick, it is logically necessary for this interior stopper to be removed before turning the container upside down, subsequently replacing the plastic stopper again to hermetically seal the container.

The problems referred to in the "Background of the Invention" section are thus solved by means of the dispenser described, as, there being no string or wick inside the compartment between the perfuming liquid and the stopper itself, the said stopper may be tightened until the mouth of the neck of the bottle or container abuts against the base of the wooden cap, so that on turning the container upside down the perfume can only flow through the narrow duct in the wooden cap and cannot reach the system whereby the cap is screwed onto the neck of the container. Logically, when the container is returned to its initial position, no perfuming liquid may seep out of the container.

DESCRIPTION OF THE DRAWINGS

To complement the description to be made hereinafter and to aid understanding of the features of the invention, according to a preferred practical embodiment thereof, a set of drawings is attached as an integral part of this description, representing the following, with an illustrative and non-limiting character.

PREFERRED EMBODIMENT OF THE INVENTION

Figure 1:
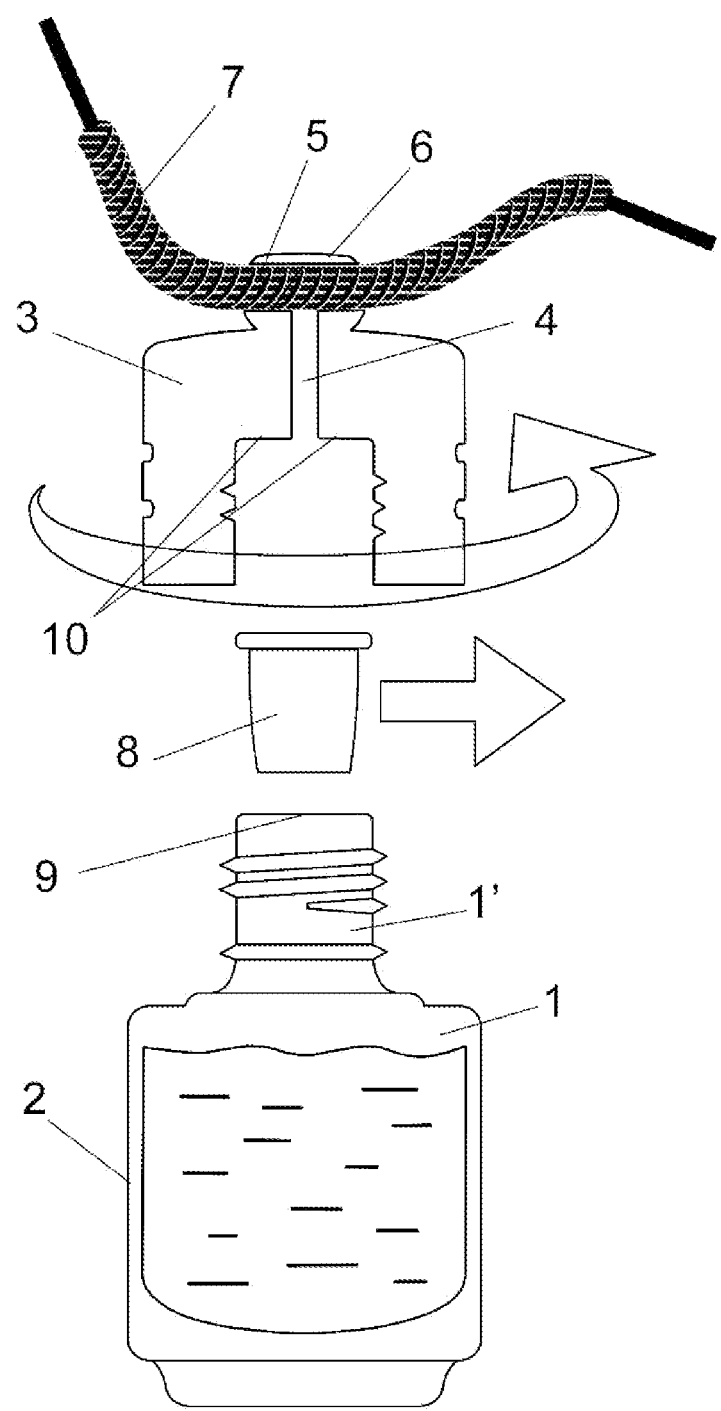
FIG. 1.—Shows an elevation view of the different parts and elements constituting the air freshener with the dispenser to which the invention relates, according to an exploded diagram.

As can be seen in the figures referred to, the dispenser to which the invention relates is intended for use with air fresheners consisting of a container (1) holding a perfuming liquid (2), which is closed by means of a wooden cap (3)

screwed onto the corresponding thread crests provided for this purpose on the neck (1') of the container (1).

The novelty of the invention lies in the fact that the wooden cap (3) includes a central axial duct (4) of small diameter, the upper part of which opens onto a transversal duct (5) corresponding to a cylindrical upper extension (6), on which the string acting as a diffuser wick (7) is located.

The unit is also complemented by a closure stopper (8), preferably made of plastic, housed inside the neck (1') of the container (1) to hermetically seal the said container when the air freshener is not in use, it being necessary to remove the said hermetic sealing stopper (8) before turning the container (1) upside down in order to impregnate the string or diffuser wick (7) with the perfuming liquid (2).

Figure 2:
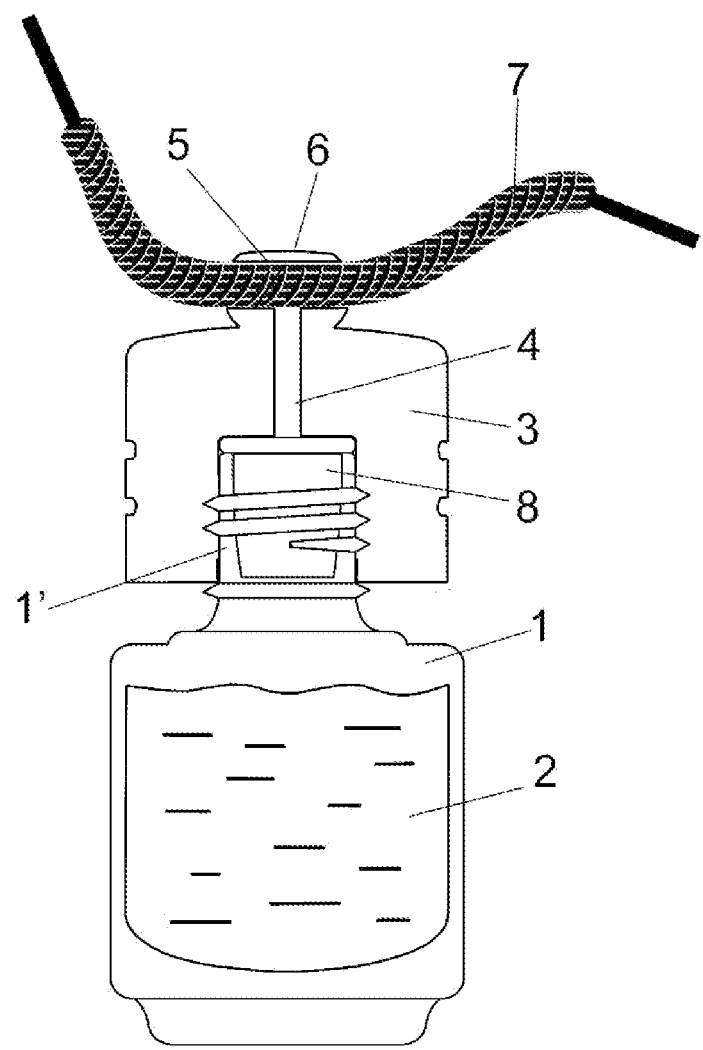
FIG. 2.—Shows the set of elements and parts represented in the previous figure, coupled together or assembled.

Thus, in the air freshener's normal position for transportation or storage, the sealing stopper (8) will remain as shown in FIG. 2, fulfilling its function of hermetically sealing the container (1).

Figure 3:
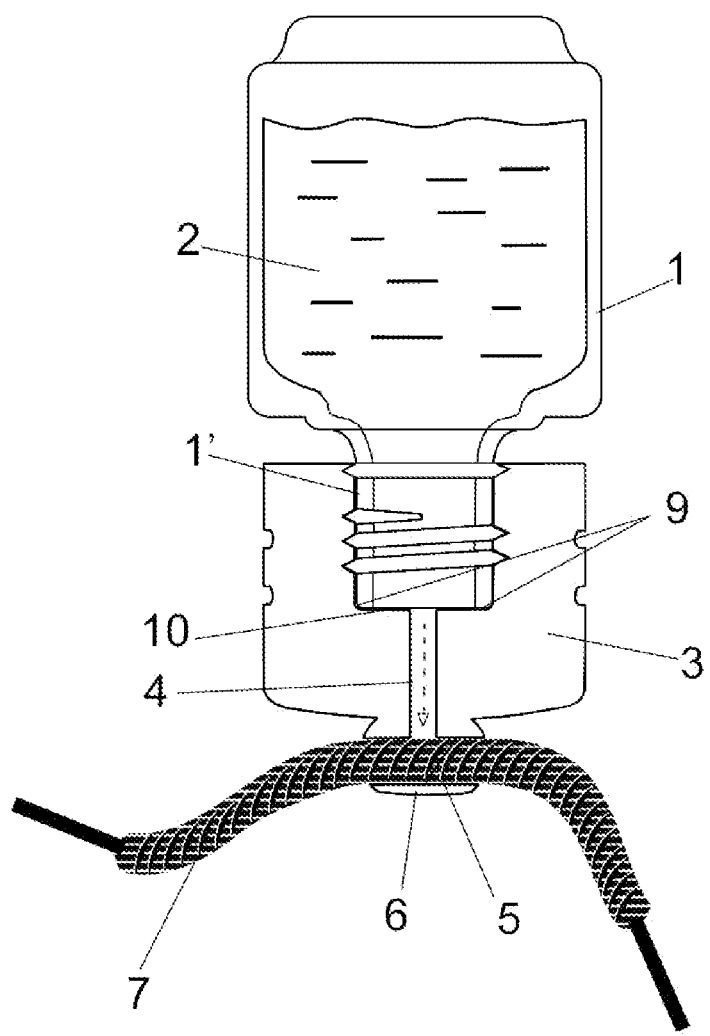
FIG. 3.—Shows an upside down view of the container, without its sealing stopper, in order to show how the perfuming liquid flows towards the actual diffuser wick or string.
Figure 4:
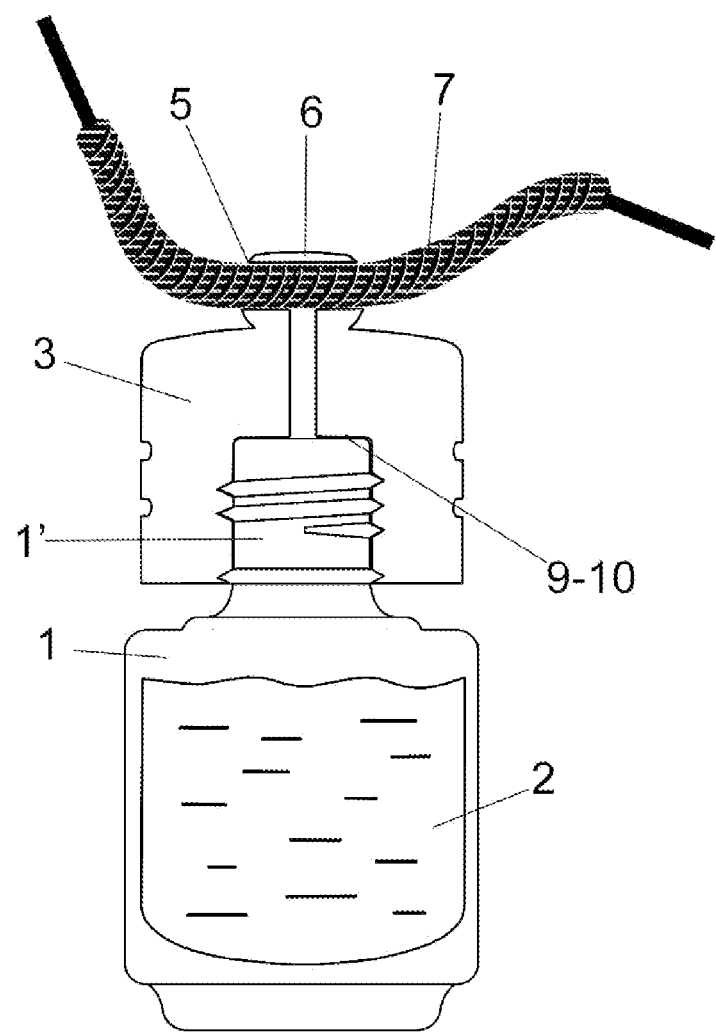
FIG. 4.—Shows a view in standard use position, without the sealing stopper.

When the air freshener is to be used, the container (1) must be turned upside down, as shown in FIG. 3, after previously having removed the sealing stopper (8), in which case when the container is turned upside down the perfuming liquid (2) reaches the duct (4), flowing through the same until it reaches the transverse duct (5) in the cylindrical end extension (6), impregnating the diffusing string or wick (7) with the perfuming liquid, so that in this upside down position the wooden cap (3) can be completely screwed onto the neck (1') of the container (1) until the upper edge (9) of the neck (1') abuts against the base (10) of the wooden cap (3), as shown in FIGS. 2, 3 and 4.

In this upside down position, the perfuming liquid (2) thus reaches the diffusing string or wick (7) due to the said perfuming liquid (2) flowing through the duct (4) in the cap (3) and through the transverse duct (5) in the upper cylindrical extension (6), the said diffusing string or wick (7) absorbing the drops of liquid that have flowed through the duct (4).

Finally, once the diffusing string or wick (7) has been impregnated, the unit is returned to its normal position, that is, the container (1) is inverted to upright position again, enabling the unit to be hung from the diffusing string or wick (7) itself, or the container (1) to be placed on any surface, allowing it to perfume the air in the enclosed space in which it is placed.

The invention claimed is:

1. An air freshener dispenser comprising:
   a container, having a neck, holding a perfuming liquid, the neck having an internal cavity having a first diameter;
   a wooden cap screwed onto the neck of the container;
   a diffusing string or wick for diffusing the perfuming liquid,
   wherein the wooden cap is provided with an axial central duct having a second diameter which communicates with a transverse duct provided in an upper cylindrical extension of the wooden cap, the diffusing string or wick passing through the transverse duct and protruding out of the wooden cap,
   wherein the second diameter of the axial central duct is smaller than the first diameter of the internal cavity of the neck of the container,
   wherein the dispenser is configured such that when the position of the container is inverted, the perfuming liquid reaches the diffusing string or wick by flowing through the axial central duct and through the transverse duct and the diffusing string or wick is impregnated in perfuming liquid; and
   wherein the wooden cap is screwed onto the neck of the container until an upper edge of the neck abuts against a base of the wooden cap.

2. The dispenser of claim 1, wherein the container further comprises a sealing stopper, being configured such that the sealing stopper is placed inside the neck of the container in order to form a hermetic seal for transportation or storage of the container; and
   wherein the sealing stopper is removed, before turning the container upside down to impregnate the diffusing string or wick in perfuming liquid.

* * * * *